(12) United States Patent
Solar et al.

(10) Patent No.: US 7,967,789 B2
(45) Date of Patent: Jun. 28, 2011

(54) INDEXING CELL DELIVERY CATHETER

(75) Inventors: Matthew S. Solar, Indialantic, FL (US); Kari Parmer, Melbourne, FL (US); Philip Smith, Minneapolis, MN (US); Frank Murdock, Indialantic, FL (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/502,889

(22) Filed: Jul. 14, 2009

(65) Prior Publication Data
US 2009/0275921 A1    Nov. 5, 2009

Related U.S. Application Data

(62) Division of application No. 10/282,584, filed on Oct. 29, 2002, now Pat. No. 7,575,571.

(51) Int. Cl.
*A61M 5/178*    (2006.01)
(52) U.S. Cl. ............. 604/165.01; 604/158; 604/164.01; 604/165.02; 604/165.04
(58) Field of Classification Search .................. 604/43, 604/158–180, 264
See application file for complete search history.

(56) References Cited

U.S. PATENT DOCUMENTS

| | | |
|---|---|---|
| 3,631,848 A | 1/1972 | Muller |
| 3,665,916 A | 5/1972 | Kobayashi et al. |
| 4,998,916 A | 3/1991 | Hammerslag et al. |
| 5,030,204 A | 7/1991 | Badger et al. |
| 5,052,998 A | 10/1991 | Zimmon |
| 5,102,401 A | 4/1992 | Lambert et al. |
| 5,195,993 A | 3/1993 | Gianakos |
| 5,236,424 A | 8/1993 | Imran |
| 5,290,222 A | 3/1994 | Feng et al. |
| 5,300,048 A | 4/1994 | Drewes, Jr. et al. |
| 5,383,865 A | 1/1995 | Michel et al. |
| 5,419,764 A | 5/1995 | Roll |
| 5,425,723 A | 6/1995 | Wang |
| 5,480,387 A | 1/1996 | Gabriel et al. |
| 5,545,147 A | 8/1996 | Harris |
| 5,800,409 A | 9/1998 | Bruce |
| 5,868,720 A | 2/1999 | Van Antwerp |

(Continued)

OTHER PUBLICATIONS

Brecknell, J., et al., "A Device for the Implantation of Multiple Cellular Deposits into a Large Volume of Brain from a Single Cannula Site",Experimental Neurology, 138, (1996), pp. 338-343.

*Primary Examiner* — Nicholas D Lucchesi
*Assistant Examiner* — Victoria P Campbell
(74) *Attorney, Agent, or Firm* — Scott A. Marks; Harness, Dickey & Pierce, P.L.C.

(57) ABSTRACT

An insertion device with an insertion axis includes an axial actuator with a first portion and a second portion. The first portion is moveable along the insertion axis relative to the second portion. The insertion device further includes a first tube coupled to the first portion of the axial actuator, and the first tube is movable along the insertion axis in response to movement of the first portion relative to the second portion. The device further includes a second tube having a radially biased distal end. The distal end is substantially contained within the first tube in a first state, and the second tube is rotatable with respect to the first tube. Also, the second tube is axially movable to a second state, and a portion of a distal end of the second tube is exposed from a distal end of the first tube in the second state.

23 Claims, 12 Drawing Sheets

U.S. PATENT DOCUMENTS

| | | | |
|---|---|---|---|
| 6,063,099 A | 5/2000 | Danks et al. | |
| 6,126,633 A | 10/2000 | Kaji et al. | |
| 6,132,390 A | 10/2000 | Cookston et al. | |
| 6,152,913 A | 11/2000 | Feith et al. | |
| 6,156,027 A | 12/2000 | West | |
| 6,171,277 B1 | 1/2001 | Ponzi | |
| 6,203,526 B1 | 3/2001 | McBeth et al. | |
| 6,206,885 B1 | 3/2001 | Ghahremani et al. | |
| 6,217,554 B1 * | 4/2001 | Green | 604/164.01 |
| 6,217,557 B1 | 4/2001 | Håkansson et al. | |
| 6,221,059 B1 | 4/2001 | Chiang et al. | |
| 6,224,588 B1 | 5/2001 | Jentzen | |
| 6,353,762 B1 | 3/2002 | Baudino et al. | |
| 6,902,569 B2 * | 6/2005 | Parmer et al. | 606/108 |
| 7,497,863 B2 * | 3/2009 | Solar et al. | 606/130 |
| 7,559,935 B2 * | 7/2009 | Solar et al. | 606/130 |
| 7,575,571 B2 * | 8/2009 | Solar et al. | 604/264 |
| 2001/0000041 A1 | 3/2001 | Selmon et al. | |
| 2002/0049451 A1 * | 4/2002 | Parmer et al. | 606/108 |
| 2002/0062143 A1 | 5/2002 | Baudino et al. | |
| 2003/0187459 A1 * | 10/2003 | Solar et al. | 606/129 |
| 2007/0250077 A1 * | 10/2007 | Skakoon et al. | 606/130 |

\* cited by examiner

INDEXING CELL DELIVERY CATHETER

CROSS-REFERENCE TO RELATED APPLICATIONS

This application is a divisional application of U.S. patent application Ser. No. 10/282,584 filed on Oct. 29, 2002. The entire disclosure of the above application is incorporated herein by reference in its entirety.

FIELD

The following relates to medical devices. Specifically, but not by way of limitation, the following relates to medical devices for introduction of a media such as cells into a body cavity, such as within the human brain.

INTRODUCTION

In this document, the medical device that is described is inserted within a body cavity. While the insertion procedure could be directed at any of several locations within a patient, for the discussion in this document, a neurosurgical procedure will be used as an example. Assisting devices may also be used in combination with the present insertion device in a neurosurgical procedure. Such devices may include, but are not limited to, a stereotactic headframe, a trajectory guide, electronic tissue imaging equipment, and frameless reference systems.

A common surgical technique inserts a medical device into a patient to a targeted area through a small opening that is surgically opened in the patient. Inserting a device to the targeted area of the patient and disturbing as little tissue as possible is a high priority. Small openings are desirable because they are less invasive and less traumatic to the patient. A catheter is a broad category of medical devices that can be inserted into a patient through small openings. The term catheter could include several configurations of devices. In one basic form, a catheter includes a hollow tube, or passage to deliver a media such as a drug or other treatment media to a selected location in the patient. Included in the general definition of catheters are multiple tube devices. Multiple tube configurations typically include an outer tube, and an inner tube, where one of the tubes is moveable with respect to the other tube.

In this document, references to coordinates with respect to catheters or insertion devices will refer to axial or longitudinal locations and radial locations. Axial or longitudinal locations are typically locations with reference to an insertion axis. Radial locations will use the conventional 2-dimensional radial coordinates (r, θ) in a circle that is normal to the insertion axis. By combining an axial coordinate with the radial coordinates, a point can be located in three dimensional space relative to a given reference frame, such as the patient. Descriptions of the insertion axis in this document will generally refer to depth inside a patient along a line. It should be noted that although catheters need not be inserted along a straight line, a generally linear depth model will be used for ease of discussion. Also, the axial end, or tip of the catheter that is inserted into a patient is referred to herein as the distal end of the catheter, while the axial end of the catheter that remains toward the outside the patient is referred to as the proximal end.

In some medical procedures, it is desirable to distribute a media over a large target area within a patient. One procedure that utilizes a large distribution target area is neurosurgical cell therapy. Several prior approaches have been used to accomplish a large distribution target area. In one approach, a relatively small catheter, such as a single lumen catheter, is inserted into a patient several consecutive times. In this procedure, a measured amount of media, or dose, is delivered at one location, and then the catheter is withdrawn and re-inserted at a nearby location to deliver another dose. This process is repeated a number of times until the entire target area has received the desired dose. A problem with this approach is that multiple insertions disturb a large amount of tissue in the patient. Each time that tissue is disturbed, there is a chance for tissue damage.

Some catheters utilize a single lumen host catheter that houses a delivery catheter having a deflected distal tip. The deflected distal tip exits the single lumen host catheter in a direction chosen by the orientation of the single lumen host catheter upon insertion. The deflected distal tip slightly increases the distribution of a single insertion and dose, however larger target area coverage is still needed. Steerable catheters exist, where the orientation and location of the distal tip can be changed while the distal tip is inserted in the patient, however, moving the distal tip while it is within the patient further disturbs tissue, which again, can lead to tissue damage. Also, steerable catheters are typically more complex and expensive to manufacture.

Another approach has been to insert a relatively large host catheter, the host catheter incorporating a number of internal passages for micro-catheters. The internal passages exit a distal end of the large host catheter at a distribution of locations around the distal end. Using this approach, the large host catheter is inserted in a center of the target area. Micro-catheters are then inserted in the various internal passages, and a dose is delivered at each of the distribution of locations. In this way a larger target area is covered without the need for multiple host catheter insertions. A problem with this approach is that the large host catheter displaces a large amount of tissue, even though the number of insertions is reduced.

What is needed is a device and method for distributing a media over a large target area. What is further needed is a device and method that disturbs a lower amount of tissue.

SUMMARY

This section provides a general summary of the disclosure, and is not a comprehensive disclosure of its full scope or all of its features.

An insertion device with an insertion axis is also disclosed. The insertion device includes an axial actuator with a first portion and a second portion, and the first portion is moveable along the insertion axis relative to the second portion. The insertion device further includes a first tube coupled to the first portion of the axial actuator, and the first tube is movable along the insertion axis in response to movement of the first portion relative to the second portion along the insertion axis. The device further includes a second tube having a radially biased distal end. The distal end of the second tube is substantially contained within the first tube in a first state, and the second tube is rotatable with respect to the first tube. Also, the second tube is axially movable to a second state, and a portion of a distal end of the second tube is exposed from a distal end of the first tube in the second state.

Additionally, an insertion device having an insertion axis is disclosed. The insertion device includes an axial actuator with a first portion and a second portion, and the first and second portions are moveably coupled. The insertion device includes a user control that selectively moves the first portion relative to the second portion axially along the insertion axis.

The device further includes a cannula including a first passage and a fixing device that selectively fixes the cannula to the first portion of the axial actuator to move the first portion and the cannula as a unit axially along the insertion axis. Moreover, the device includes a catheter with a second tube. The second tube has a distal end that is biased radially away from the insertion axis, and the second tube is received within the first passage. The catheter is rotatable about the insertion axis relative to the cannula. Also, the catheter is axially moveable along the insertion axis relative to the cannula between a first state and a second state. The distal end is contained within the first passage in the first state, and the distal end is exposed from the first passage in the second state. Furthermore, the device includes a depth adjustment actuator that selectively engages the catheter to selectively maintain the catheter in a substantially fixed axial position relative to the cannula.

An insertion device with an insertion axis is disclosed that includes an axial actuator with a first portion and a second portion. The first portion receives the second portion. Also, the second portion includes an external threading, and the first portion includes a recess. Furthermore, the device includes a user control contained within the recess between the first portion and the second portion. The user control is threadably coupled to the second portion, and the user control selectively and threadably moves the first portion relative to the second portion along the insertion axis. Furthermore, the device includes a cannula with a first passage and a fixing device that selectively fixes the cannula to the first portion of the axial actuator to move the first portion and the cannula as a unit axially along the insertion axis. The device additionally includes a microcatheter with a second tube. The second tube has a radially biased distal end. The distal end is substantially contained within the first passage in a first state. Also, the second tube is rotatable with respect to the first passage. The second tube is axially moveable along the insertion axis to a second state. Moreover, a portion of the distal end of the second tube is exposed from a distal end of the first passage in the second state. In addition, the device includes a depth adjustment actuator that selectively engages the microcatheter at a plurality of discrete axial increments to selectively maintain the second tube in a plurality of discrete axial positions between the first and second states.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected exemplary embodiments and not all possible implementations, and are not intended to limit the scope of the present disclosure.

FIG. 1b shows a cross section of the insertion device from FIG. 1a.

FIG. 4b shows a top view of the portion of the insertion device from FIG. 4a.

FIG. 5b shows a cross sectional view along line 5b-5b of the portion of the insertion device from FIG. 5a.

FIG. 6b shows an elevational view of the insertion device from FIG. 6a.

FIG. 6c shows a top view of the insertion device from FIG. 6a.

Corresponding reference numerals indicate corresponding parts throughout the several views of the drawings.

DETAILED DESCRIPTION

Exemplary embodiments will now be described more fully with reference to the accompanying drawings.

Figure 1A:
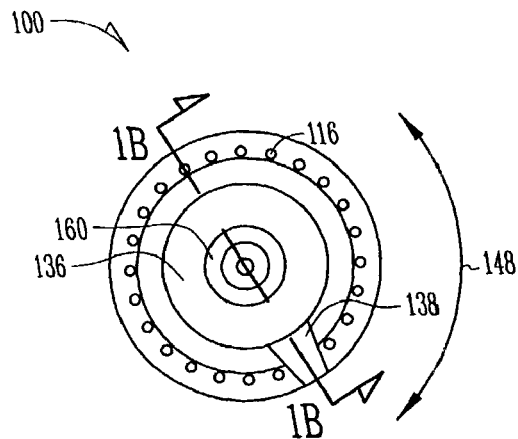
FIG. 1a shows a top view of an embodiment of an insertion device.

FIG. 1a shows a insertion device 100 according to one embodiment. The insertion device 100 in FIG. 1a is further shown in a sectional view as FIG. 1b, the section being taken along line 1b-1b.

Figure 1B:
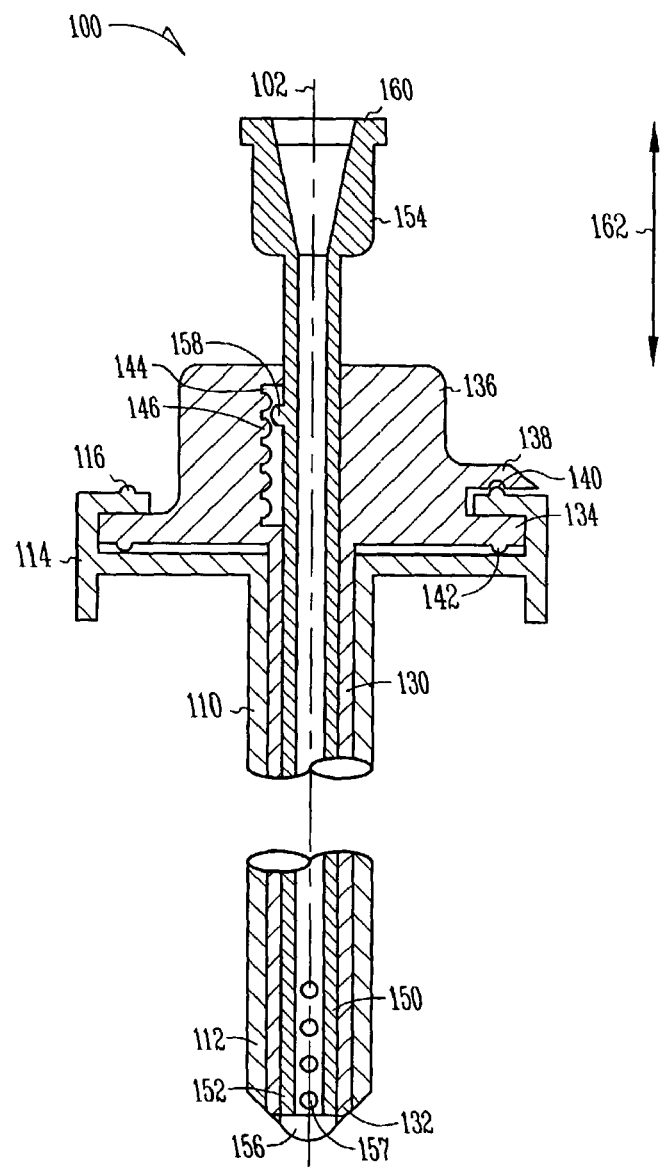

The insertion device 100 includes a first tube 110, the first tube having a distal end 112 and a proximal end 114. Located on an upper surface of the proximal end 114 are a number of first indexing bumps 116. A central axis 102 is shown in FIG. 1b. The central axis 102 in this figure represents a central axis of the first tube. In one embodiment, the central axis 102 of the first tube is the same axis as an insertion axis of the insertion device 100.

The insertion device 100 further includes a second tube 130. The second tube 130 includes a distal end 132 and a proximal end 134. The proximal end 134 of the second tube 130 includes a knob portion 136, an indexing indicator 138 with a first index engaging recess 140, and a number of friction bumps 142. The proximal end 134 of the second tube 130 also includes a recess portion 144 that contains a number of second indexing bumps 146. The second tube 130 includes a first range of motion 148 with respect to the first tube 110 as shown by the arrows 148. In one embodiment, the friction bumps 142 interact with a surface of the first tube 110 to provide a designed level of resistance to rotation within the first range of motion 148. In one embodiment, a central axis of the second tube 130 is coaxial with the central axis 102.

The first range of motion 148 is adjustable to select a radial direction, theta ($\theta$). The second tube 130 is rotatable about the first range of motion 148 with respect to the first tube 110. In one embodiment, the second range of motion is indexed by elements such as first indexing bumps 116, which interact with the first index engaging recess 140 of the indexing indicator 138. Non-indexed embodiments of the first range of motion are also contemplated within the scope of the invention. An indicating scale may also be included on the insertion device 100 to indicate the position of the third tube 150, or second tube 130, or both within the first range of motion 148. In one embodiment, the indexing indicator 138 and its associated first index engaging recess 140 combine with the first indexing bumps 116 to serve as an indicator scale in addition to serving an indexing function.

The insertion device 100 further includes a third tube 150. The third tube 150 includes a distal end 152 and a proximal end 154. The distal end 152 of the third tube 150 includes a tip portion 156, and a number of distribution holes 157. In one embodiment, the tip portion 156 is blunt to protect tissue during insertion of the insertion device 100. Along a sidewall of the third tube 150 is a second index engaging bump 158. At the proximal end 154 of the third tube 150 is a connector 160, which in one embodiment includes a luer hub configuration. The connector 160 is adapted for connection to a media source. The third tube 150 includes a second range of motion 162 with respect to the first tube 110 as shown by the arrows 162. In one embodiment, a central axis of the third tube 150 is coaxial with the central axis 102.

In one embodiment the third tube includes a coating (not shown) on an inner surface. The coating may include, but is not limited to a hydrophobic material, a hydrophilic material, or a biological agent. The biological agent may include a substance that promotes cell viability. In one embodiment where the media includes cells, the viability promoting biological coating helps to keep the cells alive for effective treatment at a target location within a patient.

Figure 1C:
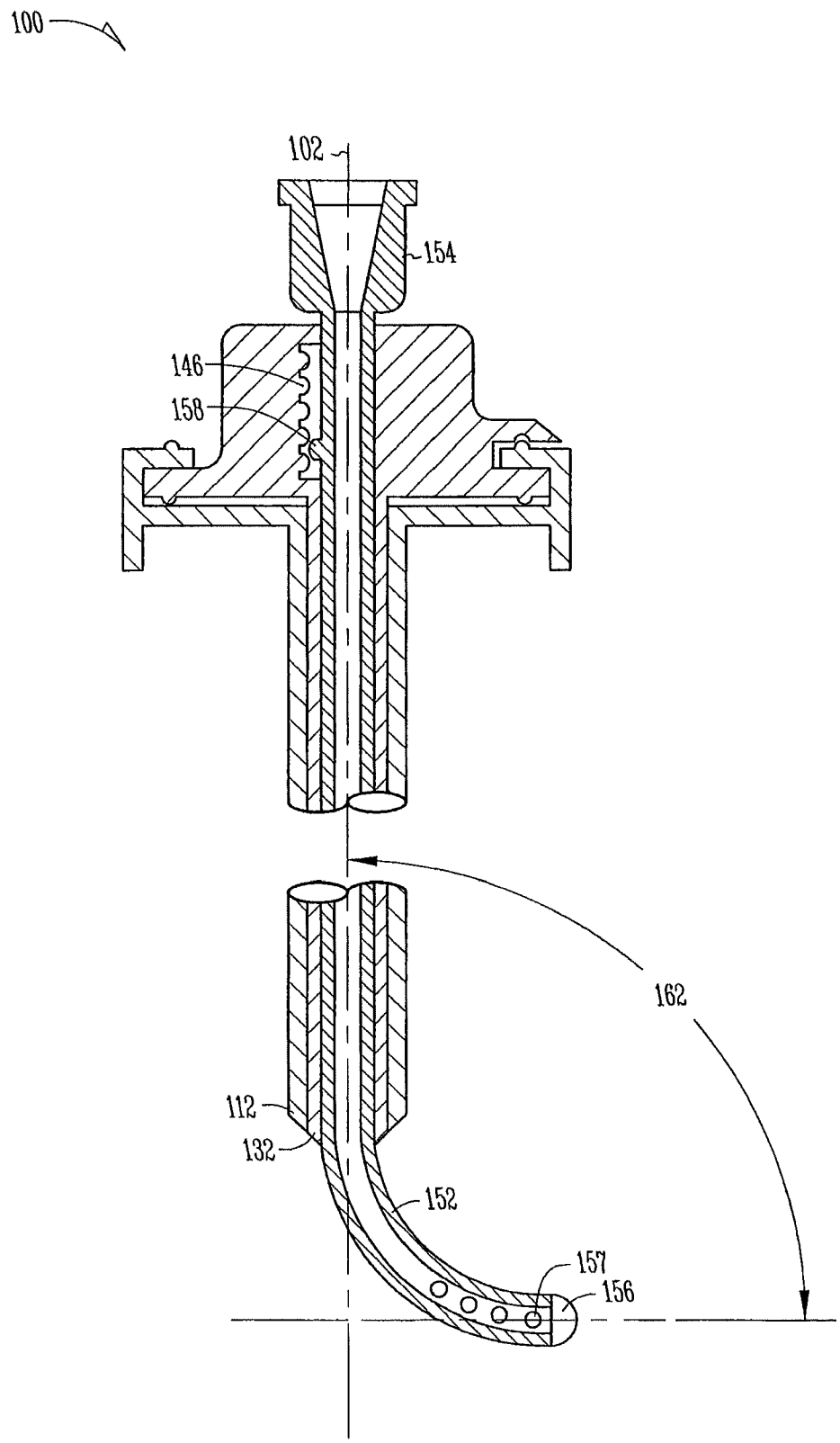
FIG. 1c shows a cross section of the insertion device from FIG. 1a in a further configuration.

FIGS. 1a and 1b illustrate the insertion device 100 in a configuration with the third tube 150 in a retracted state along the second range of motion 162. In the retracted state along the second range of motion 162, the second index engaging bump 158 is in an upper location within the number of second indexing bumps 146. FIG. 1c shows the insertion device 100 with the third tube 150 in an extended state along the second range of motion 162. In the extended state along the second range of motion 162, the second index engaging bump 158 is in a lower location within the number of second indexing bumps 146.

Although only two positions of the third tube 150 in the second range of motion 162 are shown, any of a number of locations along the second range of motion 162 are possible. Although in one embodiment, a feature such as second indexing bumps 146 indexes the second range of motion 162, non-indexed embodiments are also contemplated within the scope of the invention. An indicating scale may also be included on the insertion device 100 to indicate the position of the third tube 150 within the second range of motion 162. One example would include a series of marks on the side of the third tube to indicate a position along the second range of motion.

The distal end 152 of the third tube 150 extends radially as well as axially in the extended state. A magnitude of radial extension in one embodiment is controlled by position of the third tube 150 along the second range of motion 162. In one embodiment a magnitude of axial extension is also controlled by position of the third tube 150 along the second range of motion 162. In FIG. 1c, a configuration of the distal end 152 of the third tube 150 controls both the axial and radial components of the extension of the distal end 152.

In one embodiment, the distal end 152 extends in an arc. One skilled in the art will recognize that shapes other that an arc would also be within the scope of the invention. The radial extension component of the distal end 152 can be measured in part by an angle 162. Angle 162 is defined as the internal angle between the central axis 102 and the distal end 152 of the third tube 150 as shown in FIG. 1c. In one embodiment the arc at the distal end 152 of the third tube 150 is biased or molded permanently into the third tube. In one embodiment, the bias of the third tube is overcome by a stiffness of the second or first tube or both when the third tube is in its retracted state as shown in FIGS. 1a and 1b. In one embodiment, the third tube 150 is therefore coaxial with the central axis 102 in the retracted state, while exhibiting a radial component outward from the central axis 102 in the extended state. Other embodiments that impart a radial component to the distal end 152 of the third tube 150 in an extended state are also contemplated within the scope of the invention. For example, the second tube could include a deflecting tip to impart a radial component to the distal end 152.

In the extended state shown in FIG. 1c, the number of distribution holes 157 are exposed from the distal end 132 of the second tube and the distal end 112 of the first tube. This allows distribution of a media such as cells in a region that is axially spaced and radially spaced from the distal ends of the first and second tubes.

In one embodiment, the tip portion 156 is visible to the use of an electronic imaging system. During a procedure such as neurosurgery, an electronic imaging system such as magnetic resonance imaging (MRI), or computed tomography (CT), radio wave imaging, or other imaging system may be used to image the patient. With the tip portion 156 of the third tube 150 of the insertion device 100 visible to the selected imaging technique, it is possible for the surgeon to see more accurately the placement of the distal end 152 of the third tube. This makes delivery of the selected media more accurate.

In one embodiment, the insertion device 100 may be adjusted in two ranges of motion. While the second range of motion selects magnitude of extension, the first range of motion 148 is adjustable to select a radial direction, theta ($\theta$). The second tube 130 is rotatable about the first range of motion 148 with respect to the first tube 110. In one embodiment, the second range of motion is indexed by elements such as first indexing bumps 116, which interact with the first index engaging recess 140 of the indexing indicator 138. Non-indexed embodiments of the first range of motion are also contemplated within the scope of the invention. An indicating scale may also be included on the insertion device 100 to indicate the position of the third tube 150, or second tube 130, or both within the first range of motion 148. In one embodiment, the indexing indicator 138 and its associated first index engaging recess 140 combine with the first indexing bumps 116 to serve as an indicator scale in addition to serving an indexing function.

Figure 2A:
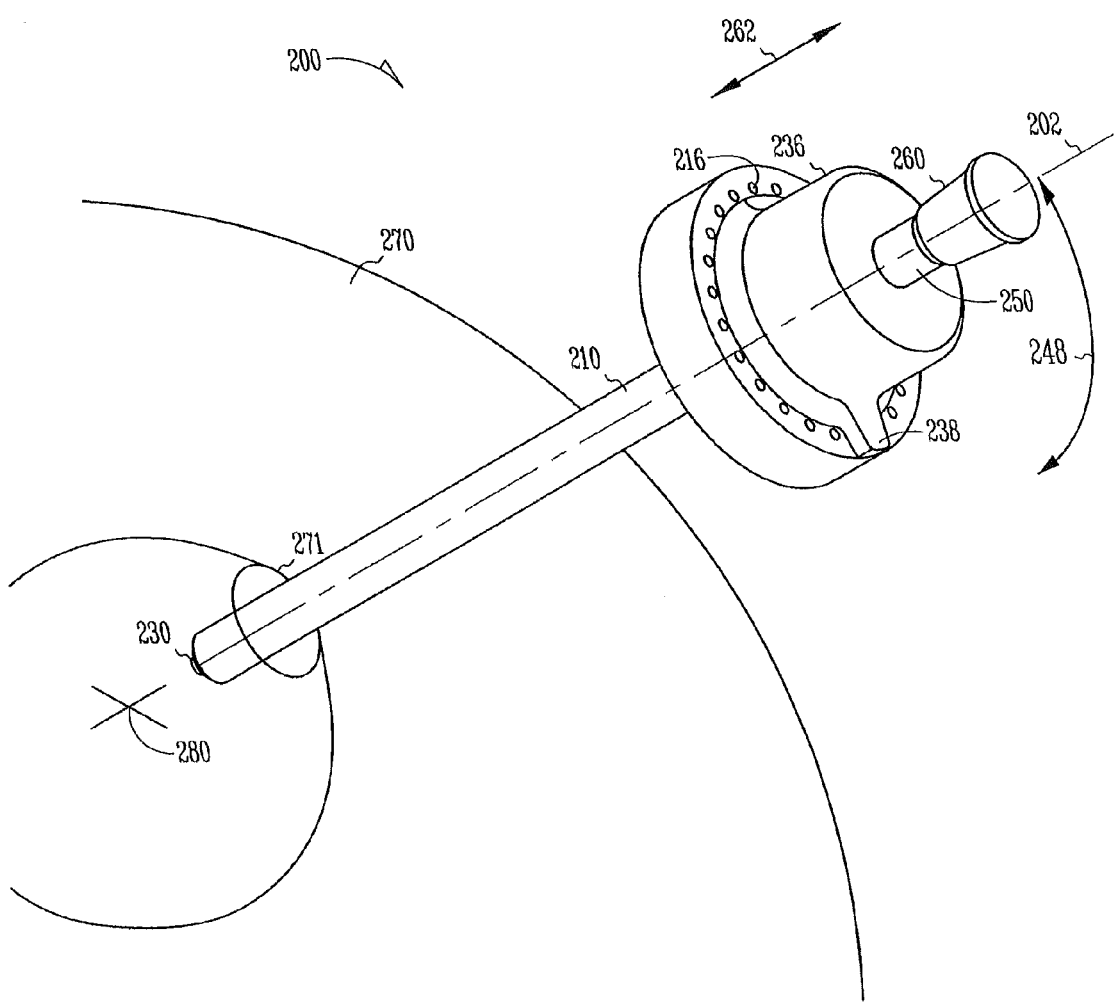
FIG. 2a shows an isometric view of an embodiment of the insertion device in one configuration.
Figure 2B:
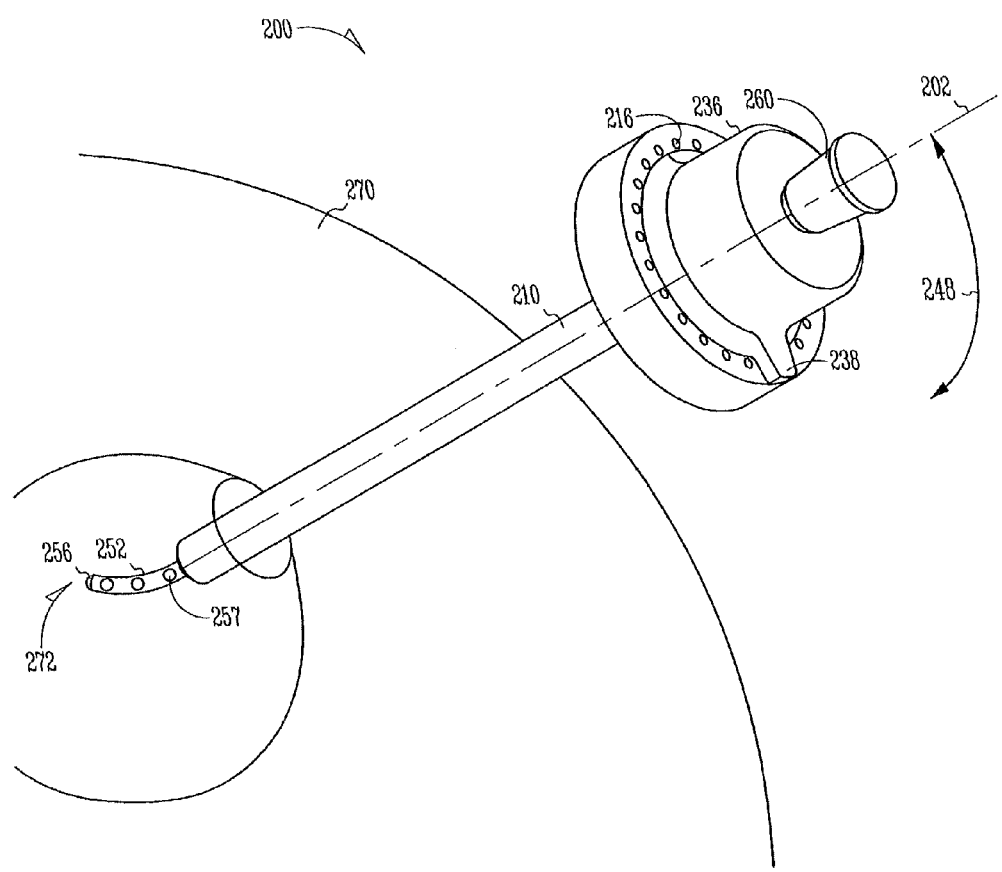
FIG. 2b shows an isometric view of an embodiment of the insertion device in another configuration.
Figure 2C:
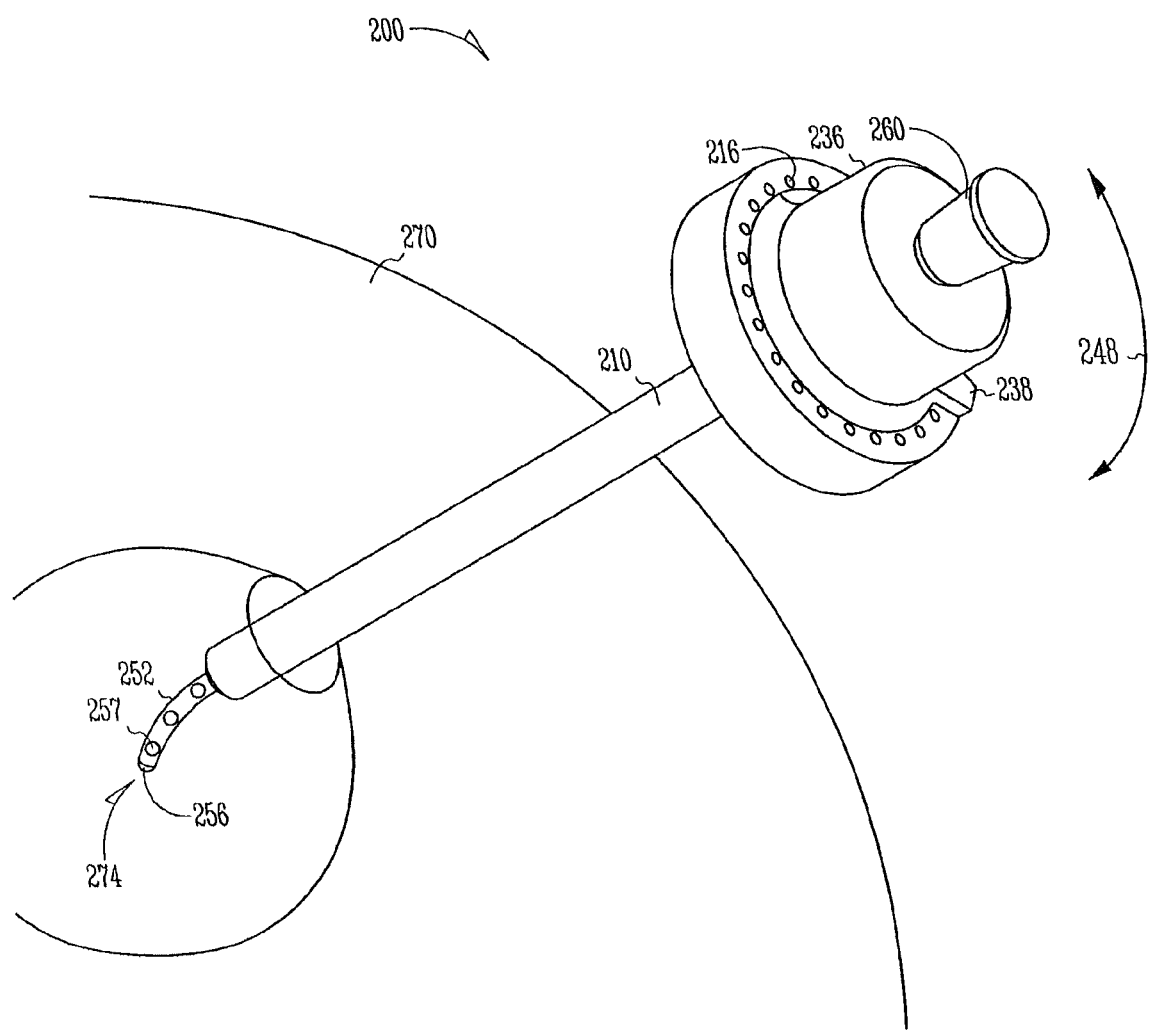
FIG. 2c shows an isometric view of an embodiment of the insertion device in another configuration.

FIGS. 2a-2c show an embodiment of a insertion device 200 in operation. The insertion device 200 in inserted into a patient 270 through an opening 271. The insertion device 200 is inserted along an insertion axis 202 to a target location 280 within the patient. Upon insertion, the insertion device 200 is in a retracted state as shown in FIG. 2a. Once the target location 280 is reached, an operator gripping a knob portion 236 and rotating a second tube 230 within a first tube 210 makes a radial selection within a first range of motion 248. In one embodiment, a third tube 250 also rotates with the second tube 230.

As shown in FIG. 2b, once the radial selection is made the third tube 250 is extended along a second range of motion 262. Extension of the third tube reveals a distal end 252 of the third tube. The distal end 252 in this embodiment is biased in an arcuate shape, therefore directing the distal end 252 of the third tube 250 outward from the insertion axis 202 in a radial direction in addition to an axial direction. Extension of the distal end 252 along the second range of motion 262, at the radial selection along the first range of motion 248, directs the distal end 252 to a first location 272. The extended distal end 252 of the third tube also exposes a number of distribution holes 257. A media source that is connected to a connector 260 such as a luer hub is then actuated to dispense a media such as cells into the patient 270 adjacent to the first location 272.

Because the distal end 252 of the third tube 250 is extended at least partially in a radial direction, rotation of the third tube 250 about the first range of motion 248 while the distal end 252 is extended could cause tissue damage. In one embodiment, the insertion device 200 includes a mechanism to prevent rotation about the first range of motion 248 while the distal tip 252 is extended. Rotation in the first range of motion 248 would be permitted once the distal end 252 is in a retracted position, and coaxial with the insertion axis 202.

After the media has been delivered to the first location 272, the third tube 250 is withdrawn back into the retracted state as shown in FIG. 2a. This is accomplished by withdrawing the third tube 250 along the second range of motion 262. The second tube is then rotated to a second radial selection within the first range of motion 248. The third tube may then be re-extended to a second location 274 within the patient 270 as shown in FIG. 2c. Once extended at the second location 274, the number of distribution holes 257 are used to distribute media such as cells to an area adjacent the second location 274.

The above detailed procedure of selection of direction, extension, distribution of media, and retraction can be repeated several times to fully cover a large area of distribution within a patient. Advantageously, the large area within the patient is covered with a single insertion of the insertion device 200. The first tube 210 in this embodiment remains stationary, and does not rotate during the procedure, while elements such as other tubes substantially contained within the first tube 210 are allowed to rotate. Thus surrounding tissue is protected during rotation from damage due to friction between surrounding tissue and the first tube 210, which is in direct contact with the surrounding tissue on a substantial portion of its side surfaces.

Although an infinite number of radial locations can be covered with this novel insertion device 200, the first tube 210 in this embodiment need only be large enough to accommodate the second and third tubes 230 and 250. The need for a large host catheter with a large number of internal passages for micro-catheters is thus eliminated. In one embodiment, when the distal end 252 of the third tube 250 is integrally molded with a bias, the need for complicated and expensive steerable catheters is also eliminated.

Indexing of the first and second ranges of motion 248 and 262 is advantageous because this allows the operator to easily adjust the various tubes of the insertion device within the first and second ranges of motion. A predetermined interval of adjustment is allocated for each index, and the operator need only adjust a number of indices for each iteration of extension/retraction as described above. In addition, the inclusion of a visible indicator scale allows the operator to see exactly where in the ranges of motion the distal end 252 of the third tube 250 is located.

The inclusion of an electronically imageable tip 256 allows the operator to use the insertion device 200 in conjunction with an imaging system such as a magnetic resonance imaging (MRI) system, or similar imaging system. Features such as indexing, visible indicator scales, and imageable tips make locating and adjusting the insertion device 200 easier, more accurate, and safer for the patient 270.

Figure 3:
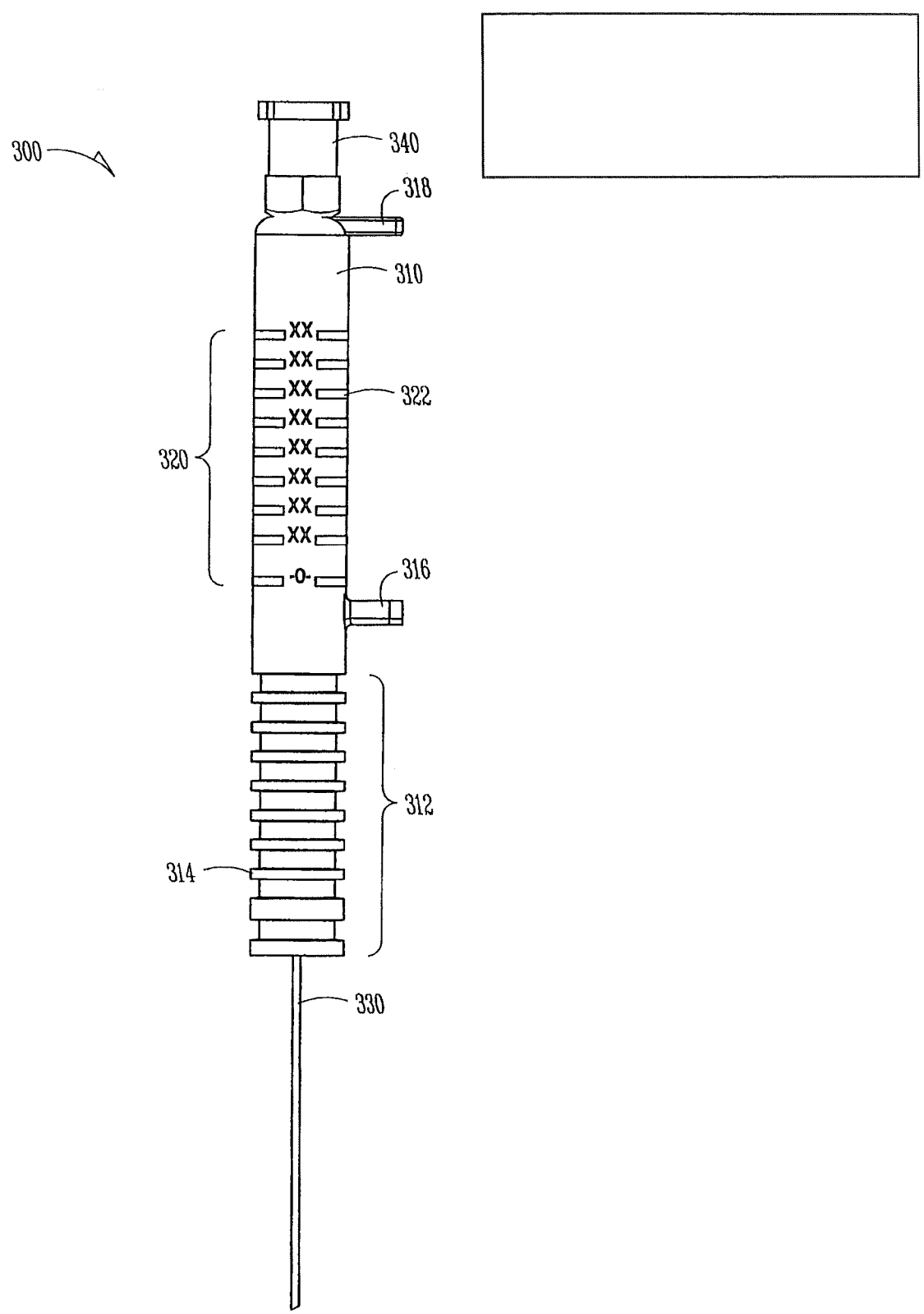
FIG. 3 shows an elevational view of a portion of an embodiment of an insertion device.

Components that are included in a further embodiment of an insertion device are shown in FIGS. 3-5b. FIG. 3 shows a microcatheter 300. The microcatheter 300 includes a proximal end portion 310 and a tube portion 330. A fitting 340 is attached to one end of the proximal end portion 310. The fitting is adapted for connection to additional devices, such as a media supply line, etc. In one embodiment, the fitting 340 includes a female luer lock fitting.

In one embodiment, a depth adjustment region 312 is included. In the embodiment shown in FIG. 3, the depth adjustment region 312 includes a number of slots 314 at varying locations along a longitudinal axis of the proximal end portion 310. One of ordinary skill in the art, with the benefit of having read the present disclosure, will recognize that alternative depth adjustment regions 312 are within the scope of the present disclosure, such as bumps, other notch profiles, or a smooth surface with a set screw, etc.

In one embodiment, an indicator scale 320 is included on the proximal end portion 310. In the embodiment shown in FIG. 3, the indicator scale 320 includes a number of marks 322 that are used to indicate a longitudinal position of the microcatheter 300 in relation to other elements of the insertion device. One of ordinary skill in the art, with the benefit of having read the present disclosure, will recognize that alternative indicator scales, including electronic position scales, etc. are within the scope of the present disclosure. In one embodiment, a rotational marker 318 is included on the proximal end portion 310. The rotational marker 318 will be described in more detail in discussion of later figures. Further included in one embodiment, an index engaging feature 316 is attached to the proximal end portion 310. The index engaging feature 316 will also be described in more detail in discussion of later figures.

Figure 4B:
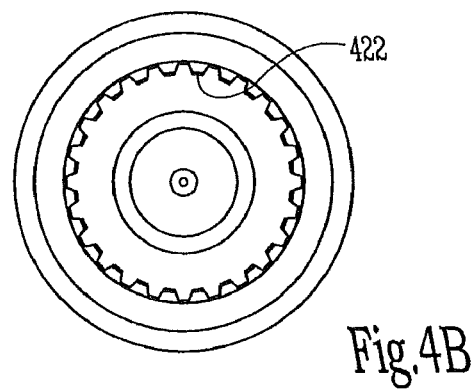
Figure 4A:
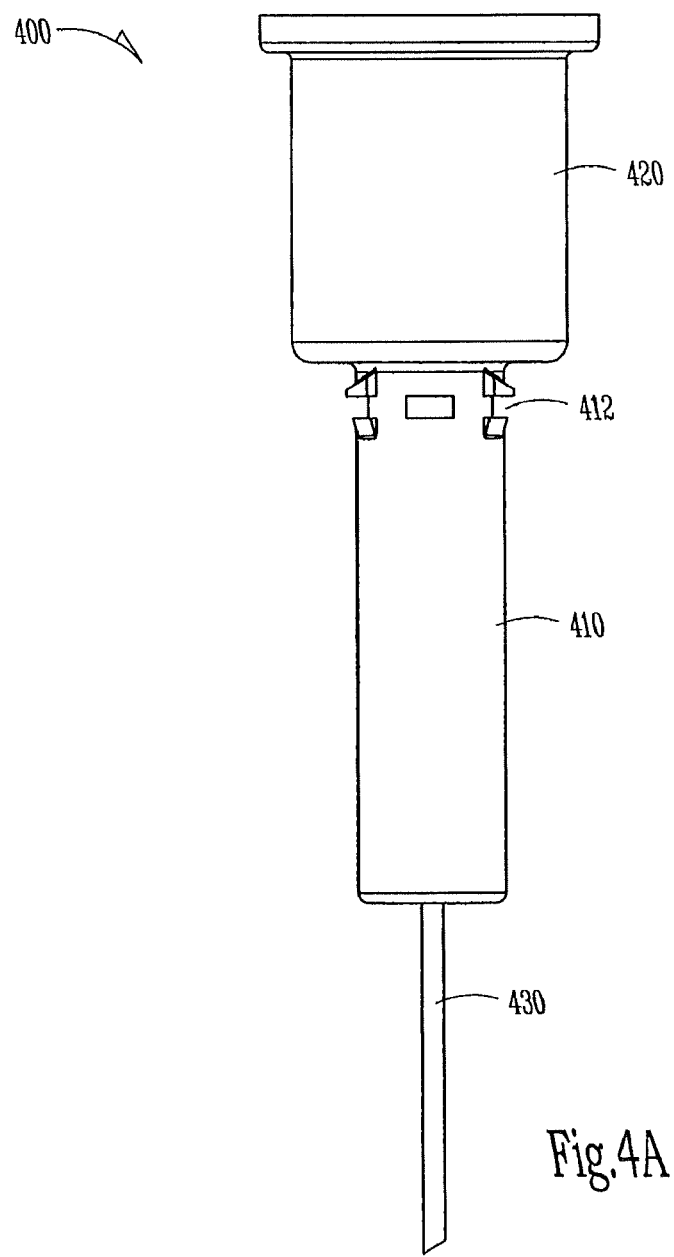
FIG. 4a shows an elevational view of another portion of an embodiment of an insertion device.

FIGS. 4a and 4b show a cannula 400. The cannula 400 includes a proximal end portion 410 and a tube portion 430. In one embodiment, the proximal end portion 410 includes an inner diameter large enough to telescope with the proximal end portion 310 of the microcatheter 300. In one embodiment, the tube portion 430 includes an inner diameter large enough to telescope with the tube portion 330 of the microcatheter 300.

The cannula 400, in one embodiment, includes an index housing 420 that includes a number of index slots 422 (FIG. 4b). One of ordinary skill in the art, with the benefit of having read the present disclosure, will recognize that any of a number of indexing devices such as ratchet shaped teeth, bumps, etc. can also be used. Also included in one embodiment of the cannula 400, is a depth adjustment actuator feature 412. The depth adjustment actuator feature 412 will be discussed in more detail in discussion of later figures.

Figure 5A:
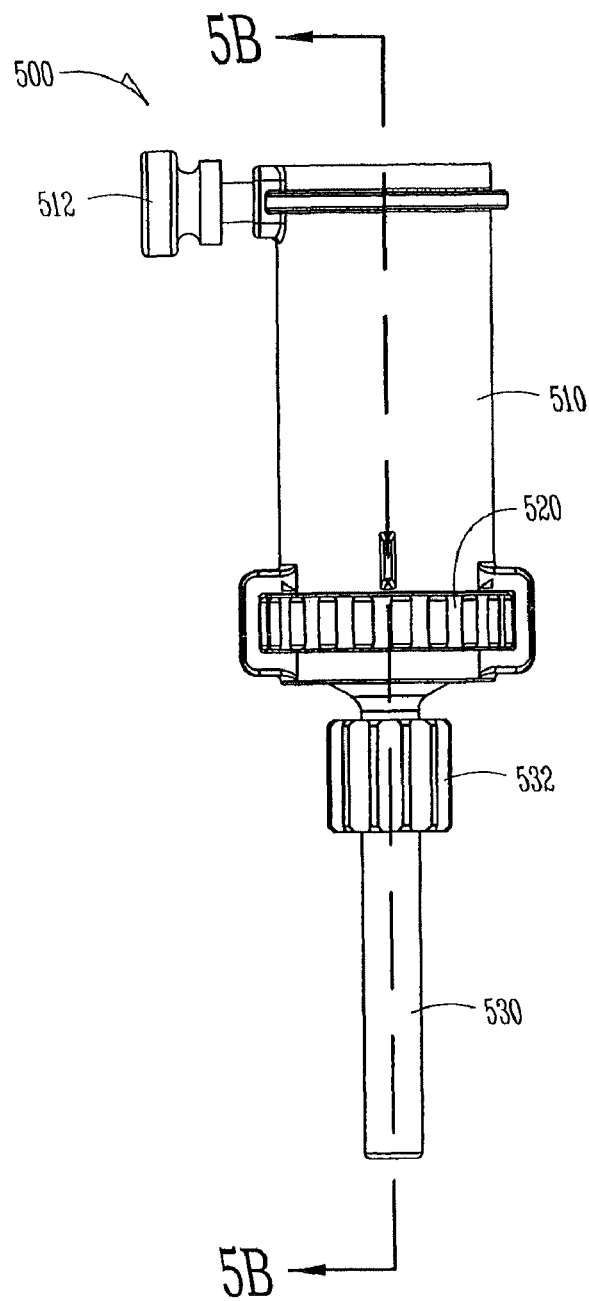
FIG. 5a shows an elevational view of another portion of an insertion device.
Figure 5B:
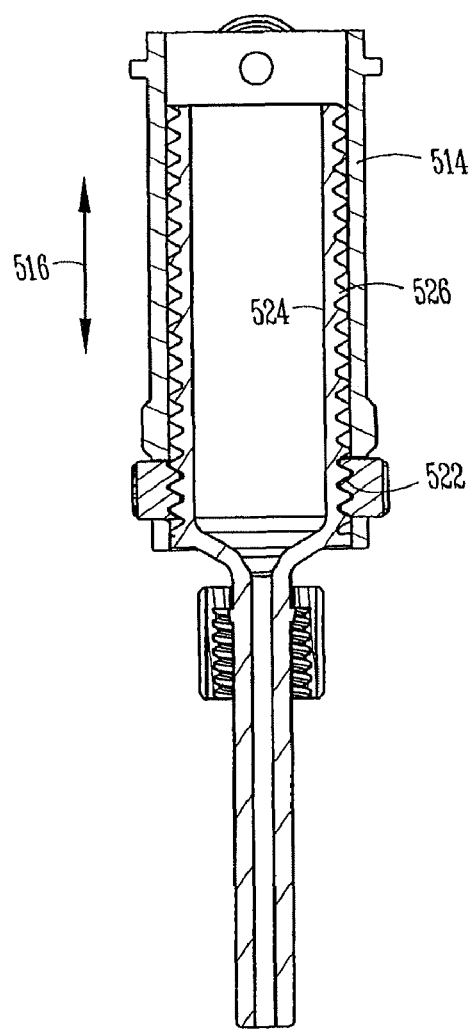

FIGS. 5a and 5b show an axial actuator 500. The axial actuator includes a main body 510 and a stem portion 530. Coupled to the stem portion 530 is a fitting 532 that is adapted for connection to additional devices that will be discussed in more detail in later figures.

In one embodiment, the main body 510 includes a first portion 514 and a second portion 524. In the embodiment shown in FIGS. 5a and 5b, the first portion 514 is axially movable with respect to the second portion 524. The relative axial motion is controlled by a user control 520. In the embodiment shown, the user control 520 includes a thumb wheel. The user control 520 includes inner threads 522 that engage a number of outer threads 526 on the second portion 524. When the user control 520 is turned, the inner threads 522 drive the outer threads 526 and the second portion 524 axially with respect to the first portion 514. The first portion 514 may in this manner be moved axially with respect to the second portion along direction 516 either apart or together depending on the direction of rotation of the user control 520. One of ordinary skill in the art, with the benefit of having read the present disclosure, will recognize that alternate axial actuator mechanisms such as a ratchet, worm thread, etc. are possible within the scope of the present disclosure.

In one embodiment, the axial actuator 500 includes a fixing device 512, such as a set screw. The fixing device 512, in one embodiment, is used to secure the proximal end portion 410 of the cannula 400 within the first portion 514 of the main body 510. In this way, the cannula 400 is axially movable by adjusting the axial actuator 500 as described above.

Figure 6A:
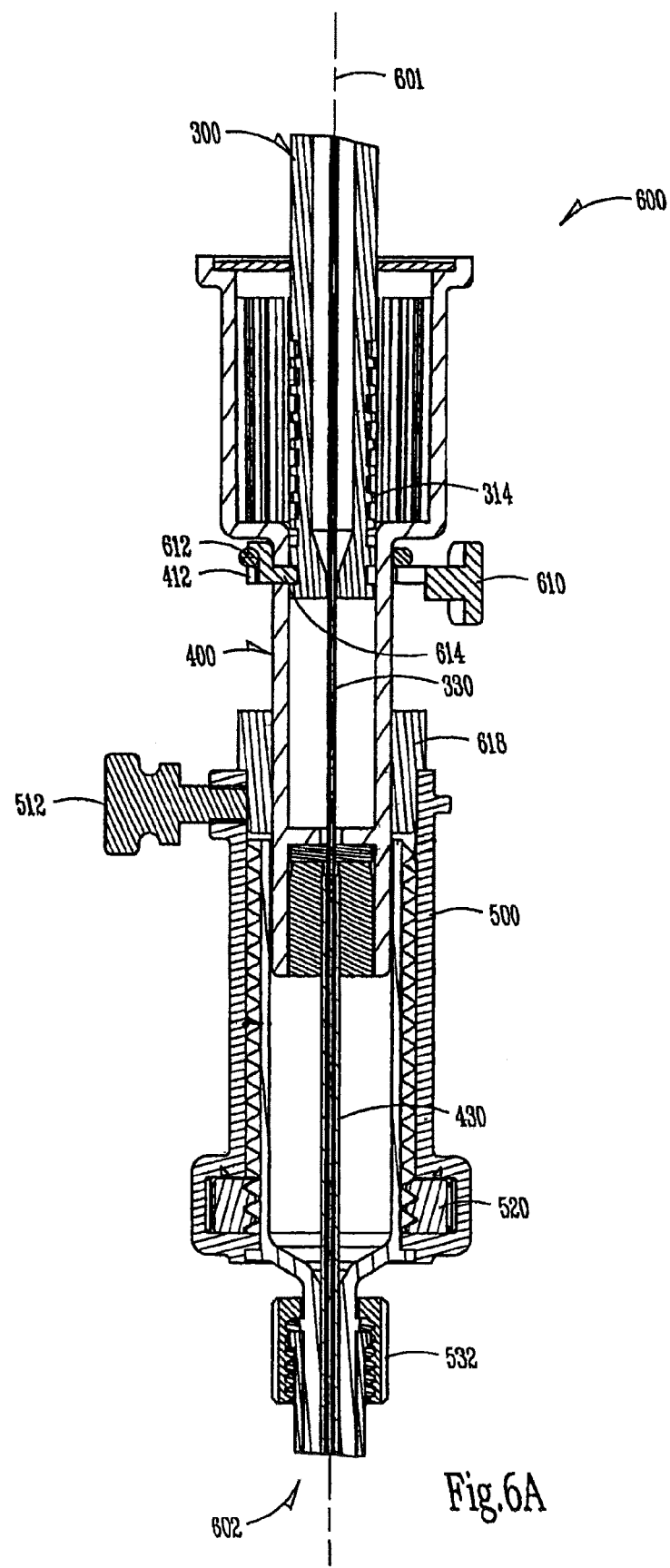
FIG. 6a shows a cross sectional view of an insertion device.

FIG. 6a shows the elements from FIGS. 3-5b coupled together in one possible configuration of an insertion device 600. The proximal end portion 310 of the microcatheter 300 is located within the proximal end portion 410 of the cannula 400. The proximal end portion 410 of the cannula 400 is further located within the main body 510 of the axial actuator 500.

A depth adjustment actuator 610 is shown adjacent to the depth adjustment actuator feature 412 of the cannula 400. The depth adjustment actuator 610 includes an engagement feature 614 and a biasing device 612 in the embodiment shown. In one embodiment, the biasing device 612 includes an elastic O-ring that fits within the depth adjustment actuator feature 412. The biasing device 612 urges the engagement feature 614 into one of the slots 314 of the microcatheter 300. As discussed above, other depth adjustment designs are also contemplated within the scope of the invention.

The fixing device 512 is shown engaging the cannula 400 through a bushing 618. The bushing 618 is included on some embodiments to further fix a maximum depth of the insertion device 600 during initial setup of the insertion device 600 in a medical procedure.

In one embodiment, the microcatheter 300 is rotatable about the insertion axis 601, and the rotation is indexed. In the embodiment shown, the index engaging feature 316 of the microcatheter engages the number of index slots 422 of the cannula 400. Rotation of the microcatheter 300, is thus divided into discrete steps in embodiments that include the indexing feature.

The tube 330 of the microcatheter is shown passing along an insertion axis 601 of the insertion device 600. The microcatheter travels inside the tube 430 of the cannula 400 as both tubes 330 and 430 exit the insertion device 600 towards a distal end 602. The tubes 330 and 430 at their distal end 602 are the portions of the insertion device that are actually placed inside a patient for a procedure such as delivery of a media.

Figure 6B:
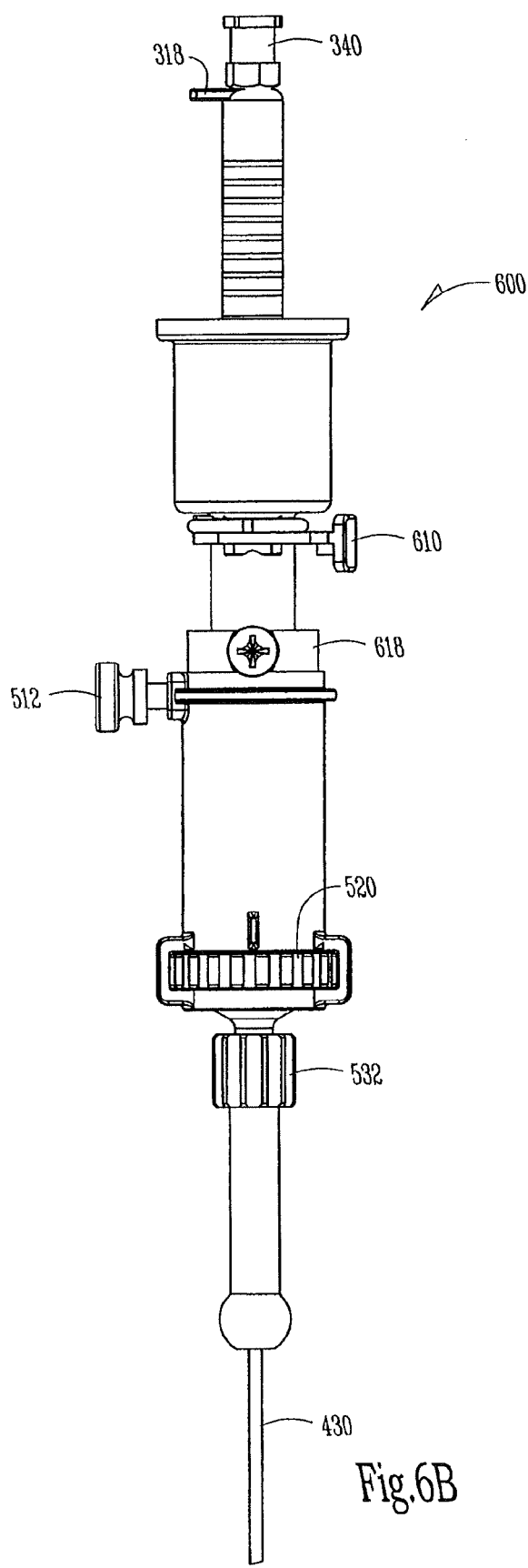
Figure 6C:
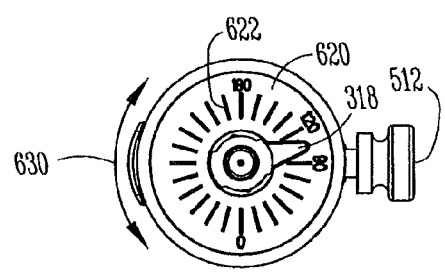

FIGS. 6b and 6c further show elements of the insertion device 600 from FIG. 6a. FIG. 6b shows the fitting 532 of the stem portion 530 attached to a portion of a trajectory device that will be discussed in later figures. FIG. 6c shows an indicator scale 620 that indicates a rotational position of the microcatheter 300 with respect to the cannula 400. A rotational range of motion of the microcatheter 300 with respect to the cannula 400 is shown by arrows 630. The indicator scale 620 includes a number of markings 622 that define exact angles of position. The rotational marker 318 is coupled to the microcatheter 300, while the indicator scale 620 is coupled to the cannula 400. In this way, the relative position of the microcatheter 300 with respect to the cannula 400 is shown. One of ordinary skill in the art, with the benefit of having read the present disclosure, will recognize that alternative indicator scales, including electronic position scales, etc. are within the scope of the present disclosure.

Figure 7A:
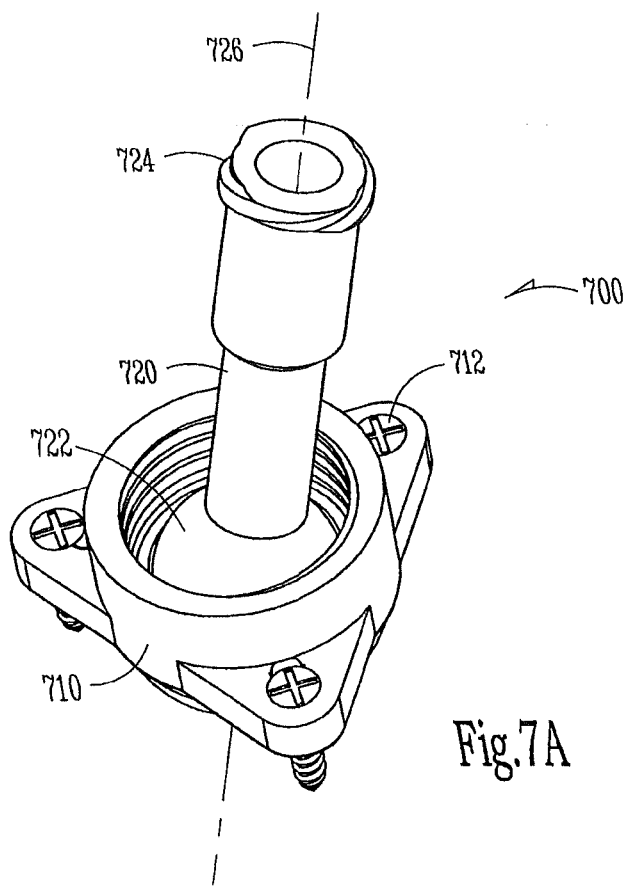
FIG. 7a shows an isometric view of a trajectory device.

FIG. 7a shows an embodiment of a trajectory guide 700. The trajectory guide 700 includes a stem portion 720. The stem portion further includes a fitting adaptor 724 such as a male luer lock, and a multi axis joint 722, such as a ball joint. The multi axis joint 722 allows adjustment of a trajectory axis 726. The trajectory guide 700 further includes a base 710 with at least one securing device 712 such as a screw.

Figure 7B:
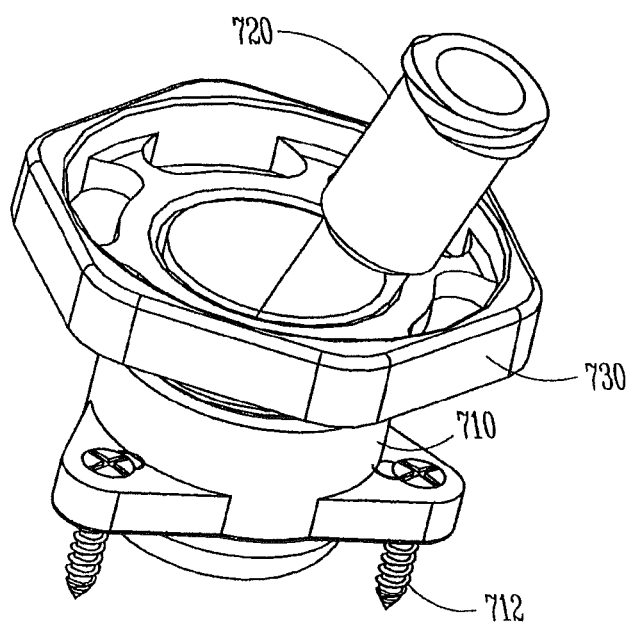
FIG. 7b shows an additional isometric view of a trajectory device.

In operation, the base 710 is attached to a patient using the securing devices 712. An example of a location on a patient includes mounting the base 710 directly to the skull of a patient. The stem 720 is then adjusted to point the trajectory axis 726 to a desired location within the patient. FIG. 7b further shows a fixing device 730 such as a locking that is used to fix the trajectory axis 726 once targeting of the desired location is complete.

The trajectory guide 700 as shown in FIGS. 7a and 7b is used in one possible embodiment an insertion device from previous figures. For example, in FIG. 6b, the fitting 532 is shown secured to a stem such as found in the trajectory guide 700. Other embodiments do not include the trajectory guide 700, and use other means to adjust a trajectory before performing an insertion procedure.

In embodiments that include a trajectory guide 700, the axial actuator 500 is secured to the trajectory guide 700 with the insertion axis 601 substantially coaxial with the trajectory axis of the trajectory guide 700. A starting condition is set by adjusting a pair of variables. The microcatheter tube 330 is secured substantially within the cannula tube 430 using the depth adjustment actuator 610, and a desired slot 314. An axial starting depth of the two tubes 330 and 430 is then set by using the fixing device 512 to secure the cannula 400 to the axial actuator 500.

The insertion microcatheter tube 330 and the cannula tube 430 are inserted into a patient through an opening or incision. The microcatheter tube 330 and cannula tube 430 are inserted along the insertion axis 601 to a target location within the patient. Insertion is accomplished by actuation of the axial actuator 500 with the user control 520. During insertion, the microcatheter tube 330 is substantially contained within the cannula tube 430. Similar to previously described embodiments, the distal end of the microcatheter tube 330 may include a blunt tip to prevent tissue damage during insertion. Once the target location is reached, an operator makes a beginning radial selection using the indicator scale 620 shown in FIG. 6c. The microcatheter tube 330 is allowed to rotate substantially within the cannula tube 430 without rotation of the cannula tube 430. Tissue surrounding the cannula tube 430 is not subject to any rotational friction from sidewalls of the cannula tube 430.

Once the radial selection is made, the microcatheter tube 330 is extended along the insertion axis 601 by itself, leaving the cannula tube 430 in place. This is accomplished by actuating the depth adjustment actuator 610, and moving to another selected slot 314. The depth of the microcatheter 330, as extended separate from the cannula tube 430, is indicated by the indicator scale 320. Again, very little tissue is disturbed due to the stationary position of the cannula tube 430.

Extension of the microcatheter tube 330 reveals a distal end of the microcatheter tube 330 with a bias as described in other embodiments above. The distal end in one embodiment is biased in an arcuate shape, therefore directing the distal end of the microcatheter tube 330 outward from the insertion axis 601 in a radial direction in addition to an axial direction.

Extension of the distal end of the microcatheter tube 330, at the beginning radial selection, directs the distal end to a first location. The extended distal end of the microcatheter tube 330 also exposes a number of distribution holes as described in embodiments above. A media source that is connected to the fitting 340 such as a luer lock hub is then actuated to dispense a media such as cells into the patient adjacent to the first location.

Because the distal end of the microcatheter tube 330 is extended at least partially in a radial direction, rotation of the microcatheter tube 330 while the distal end is extended could cause tissue damage. In one embodiment, the insertion device 600 includes a mechanism such as a selectively keyed slot, etc. to prevent rotation while the distal tip of the microcatheter tube 330 is extended.

After the media has been delivered to the first location, the microcatheter tube 330 is withdrawn substantially within the cannula tube 430. This is accomplished by using the depth adjustment actuator 610, and moving to another selected slot 314.

The microcatheter tube 330 is then rotated to a second radial selection using the indicator scale 620 shown in FIG. 6c. The microcatheter tube 330 may then be re-extended to a second location within the patient. Once extended at the second location, the number of distribution holes are used to distribute media such as cells to an area adjacent the second location.

Several iterations of moving to a new radial selection and extending the microcatheter tube 330 can be performed to reach numerous locations within the patient. Advantageously, the cannula tube remains stationary during all iterations. One depth of the cannula tube 430 along the insertion axis 601 is described in the example above, however the iterations described above can be performed at multiple cannula tube 430 depths along the insertion axis 601 to accomplish a further distribution of media. Once the media has been delivered to the desired number of locations, the microcatheter tube 330 and the cannula tube 430 are withdrawn together by actuating the user control 520 of the axial actuator 500.

Although the description of operation steps above is described in an order, other orders of operations are also possible within the scope of the invention. One of ordinary skill in the art, with the benefit of having read the present disclosure, will recognize alternative orders to accomplish the same objective.

Figure 8:
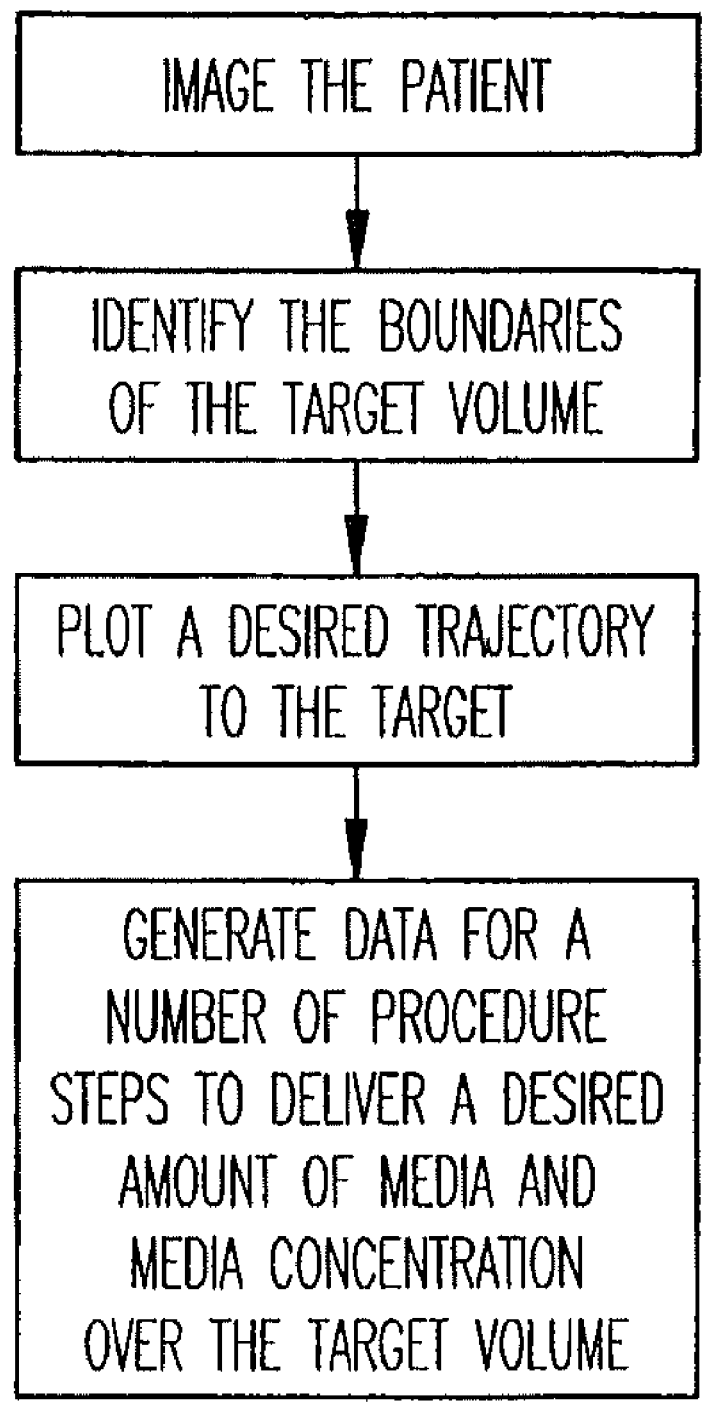
FIG. 8 shows a flowchart of a method for setting up a procedure according to one embodiment of the invention.

FIG. 8 shows a flowchart for a method of operation of an insertion device as described in embodiments above. First the patient is imaged in three dimensions using any of a number of tissue imaging techniques such as MRI, CT, PET, etc. A target volume such as a tumor, or other target volume is then identified. Boundaries of the target volume are identified and marked using, for example, computer software that interfaces with the imaging device. A trajectory is then plotted to intersect with the target volume as identified. In one embodiment, the trajectory is plotted as a part of the imaging procedure. In one embodiment the trajectory is plotted as a part of the insertion procedure. In another embodiment, imaging, plotting the trajectory, and insertion are all performed in a single procedure. One method of plotting the trajectory includes imaging an actual trajectory of a trajectory guide such as the trajectory guide shown in FIGS. 7a and 7b, the trajectory guide being mounted directly to a patient.

Using geometry, in conjunction with known values such as a starting tip location of a microcatheter, a starting tip location of a cannula, amount of bias or arc shape at a distal tip of the microcatheter, desired dose of media to be introduced, etc. a set of data can be generated for use in a procedure to introduce media to the target volume. In one embodiment, a table of instructions is generated that determines a number of steps in media delivery iterations.

By following the table of instructions for one iteration, or a number of iterations, a media concentration or concentration gradient can be effectively delivered over the target volume. A location of a distal tip of the microcatheter is determined by sets of data points in the table. For a larger target volume, a number of locations are determined by the table of instructions, and a dose of media is delivered at each of the locations. In this way a dose of media can be delivered to a large volume target area using a single insertion. In one embodiment, the table of instructions includes variables such as axial depth of the cannula, axial depth of the microcatheter, and rotational angle of the microcatheter.

Thus has been shown an insertion device and method of using and manufacturing a insertion device, wherein the insertion device is capable of distributing a media over a large distribution area inside a patient while reducing the amount of tissue disturbed by the procedure.

Although specific embodiments have been illustrated and described herein, it will be appreciated by those skilled in the art that any arrangement which is calculated to achieve the same purpose may be substituted for the specific embodiment shown. This document is intended to cover any adaptations of variations of the present invention. It is to be understood that the above description is intended to be illustrative, and not restrictive. The scope of the invention includes any other applications in which the above structures and fabrication methods are used. The scope of the invention should be determined with reference to the appended claims, along with the full scope of equivalents to which such claims are entitled.

What is claimed is:

1. An insertion device with an insertion axis, comprising:
an axial actuator with a first portion and a second portion, the first portion being moveable along the insertion axis relative to the second portion;
a first tube coupled to the first portion of the axial actuator wherein the first tube is movable along the insertion axis in response to movement of the first portion relative to the second portion along the insertion axis;
a second tube having a radially biased distal end, wherein:
the distal end of the second tube is substantially contained within the first tube in a first state;
the second tube is rotatable with respect to the first tube; and
the second tube is axially movable to a second state, a portion of a distal end of the second tube being exposed from a distal end of the first tube in the second state; and
an indexing system that allows rotational movement of the second tube relative to the first tube at discrete increments, the indexing system including at least an index engaging feature and at least one index slot that selectively receives the index engaging feature.

2. The insertion device of claim 1, further including a first indicator scale indicating a rotational position of the second tube relative to the first tube.

3. The insertion device of claim 1, further including a second indicator scale indicating an axial position of the second tube relative to the first tube.

4. The insertion device of claim 1, further including a seal between the first tube and the second tube.

5. The insertion device of claim 1, further including a trajectory guide coupled to the insertion device, the trajectory guide being adapted for direct coupling to a surface of a patient.

6. The insertion device of claim 1, wherein the distal end of the second tube is integrally molded with an arcuate shape.

7. The insertion device of claim 1, wherein the second tube includes at least one radial hole in a sidewall region for delivering a media into a body cavity.

8. The insertion device of claim 1, wherein a distal end of the second tube is blunt to protect tissue during insertion.

9. The insertion device of claim 1, including a depth adjustment actuator that allows axial movement of the second tube relative to the first tube at discrete increments.

10. The insertion device of claim 9, wherein the depth adjustment actuator includes at least one slot and at least an engagement feature that is selectively received within the at least one slot.

11. An insertion device having an insertion axis, comprising:
an axial actuator with a first portion and a second portion, the first and second portions being moveably coupled, the second portion including an outer thread;
a user control with an inner thread that threadably engages the outer thread of the second portion, the user control selectively advancing along the outer thread to selectively move the first portion of the axial actuator relative to the second portion axially along the insertion axis;
a cannula including a first tube;
a fixing device that selectively fixes the cannula to the first portion of the axial actuator to move the first portion and the cannula as a unit axially along the insertion axis;
a catheter with a second tube, the second tube having a distal end that is biased radially away from the insertion axis, the second tube being received within the first tube, the catheter being rotatable about the insertion axis relative to the cannula, the catheter being axially moveable along the insertion axis relative to the cannula between a first state and a second state, the distal end being contained within the first tube in the first state, and the distal end exposed from the first passage in the second state; and
a depth adjustment actuator that selectively engages the catheter to selectively maintain the catheter in a substantially fixed axial position relative to the cannula.

12. The insertion device of claim 11, further comprising an indexing system that allows rotation of the catheter about the insertion axis relative to the cannula at discrete increments.

13. The insertion device of claim 11, further including a first indicator scale indicating a rotational position of the second tube relative to the first tube.

14. The insertion device of claim 11, further including a second indicator scale indicating an axial position of the second tube relative to the first passage.

15. The insertion device of claim 11, further including a seal between the first and second tubes.

16. The insertion device of claim 11, further including a trajectory guide including a base to be fixed to a patient and a stem that is moveably coupled to the base, the axial actuator being removeably coupled to the stem, and the first and second tubes being received within the stem.

17. The insertion device of claim 11, wherein the distal end of the second tube is integrally molded with an arcuate shape.

18. The insertion device of claim 11, wherein the second tube includes at least one radial hole in a sidewall region for delivering a media into a body cavity.

19. The insertion device of claim 11, wherein a distal end of the second tube is blunt to protect tissue during insertion.

20. The insertion device of claim 11, wherein the fixing device includes a set screw that is operably supported on the first portion of the axial actuator.

21. An insertion device having an insertion axis, comprising:
an axial actuator with a first portion and a second portion, the first and second portions being moveably coupled;
a user control that selectively moves the first portion relative to the second portion axially along the insertion axis;
a cannula including a first tube;
a fixing device that selectively fixes the cannula to the first portion of the axial actuator to move the first portion and the cannula as a unit axially along the insertion axis;
a catheter with a second tube, the second tube having a distal end that is biased radially away from the insertion axis, the second tube being received within the first tube, the catheter being rotatable about the insertion axis relative to the cannula, the catheter being axially moveable along the insertion axis relative to the cannula between a first state and a second state, the distal end being contained within the first tube in the first state, and the distal end exposed from the first passage in the second state;
a depth adjustment actuator that selectively engages the catheter to selectively maintain the catheter in a substantially fixed axial position relative to the cannula, wherein one of the catheter and the depth adjustment actuator includes a plurality of slots and the other of the catheter and the depth adjustment actuator includes an engagement feature, the engagement feature being selectively received in one of the plurality of slots to selectively maintain the catheter in a substantially fixed axial position relative to the cannula; and
a biasing member that biases the engagement feature toward the one of the plurality of slots.

22. An insertion device with an insertion axis comprising:
an axial actuator with a first portion and a second portion, the first portion receiving the second portion, the second portion including an external threading, and the first portion including a recess;
a user control contained within the recess and being directly threadably coupled to the second portion, the user control selectively and threadably moving the first portion relative to the second portion along the insertion axis;
a cannula defining a first passage;
a fixing device that selectively fixes the cannula to the first portion of the axial actuator to move the first portion and the cannula as a unit axially along the insertion axis;
a microcatheter with a second passage, the second passage having a radially biased distal end, the distal end being substantially contained within the first passage in a first state, the second passage being rotatable with respect to the first passage, and the second passage being axially moveable along the insertion axis to a second state, a portion of the distal end of the second passage being exposed from a distal end of the first passage in the second state; and
a depth adjustment actuator that selectively engages the microcatheter at a plurality of discrete axial increments to selectively maintain the second passage in a plurality of discrete axial positions between the first and second states.

23. The insertion device of claim 22, wherein the depth adjustment actuator selectively engages the microcatheter at a plurality of fixed discrete axial increments to selectively maintain the second passage in a plurality of discrete axial positions between the first and second states.

* * * * *